(12) United States Patent
Nagy et al.

(10) Patent No.: US 7,858,718 B1
(45) Date of Patent: *Dec. 28, 2010

(54) CATALYSTS BASED ON 2-ARYL-8-ANILINOQUINOLINE LIGANDS

(75) Inventors: Sandor Nagy, Naperville, IL (US); Linda N. Winslow, Cincinnati, OH (US); Shahram Mihan, Bad Soden (DE); Reynald Chevalier, Frankfurt (DE); Lenka Lukesova, Frankfurt (DE); Ilya E. Nifant'ev, Moscow (RU); Pavel V. Ivchenko, Moscow (RU); Michael W. Lynch, West Chester, OH (US)

(73) Assignee: Equistar Chemicals, LP, Houston, TX (US)

( * ) Notice: Subject to any disclaimer, the term of this patent is extended or adjusted under 35 U.S.C. 154(b) by 37 days.

This patent is subject to a terminal disclaimer.

(21) Appl. No.: 12/460,621

(22) Filed: Jul. 22, 2009

(51) Int. Cl.
C08F 4/76 (2006.01)
C08F 4/64 (2006.01)
C08F 4/52 (2006.01)
C07F 7/00 (2006.01)

(52) U.S. Cl. .................. 526/172; 526/161; 526/134; 526/348; 526/348.2; 526/348.5; 526/348.6; 526/351; 526/352; 526/901; 526/941; 556/52; 556/51; 502/103

(58) Field of Classification Search .................. 556/52; 502/103; 526/172, 161
See application file for complete search history.

(56) References Cited

U.S. PATENT DOCUMENTS

| | | | |
|---|---|---|---|
| 5,153,157 A | 10/1992 | Hlatky et al. | |
| 5,198,401 A | 3/1993 | Turner et al. | |
| 5,241,025 A | 8/1993 | Hlatky et al. | |
| 5,414,180 A | 5/1995 | Geerts et al. | |
| 5,637,660 A * | 6/1997 | Nagy et al. | .................. 526/160 |
| 5,648,440 A | 7/1997 | Sugano et al. | |
| 5,889,128 A | 3/1999 | Schrock et al. | |
| 6,103,657 A | 8/2000 | Murray | |
| 6,211,311 B1 | 4/2001 | Wang et al. | |
| 6,271,323 B1 | 8/2001 | Loveday et al. | |
| 6,653,417 B2 | 11/2003 | Peterson | |
| 6,706,829 B2 | 3/2004 | Boussie et al. | |
| 6,939,969 B2 * | 9/2005 | Peters et al. | .................. 546/171 |
| 6,953,764 B2 | 10/2005 | Frazier et al. | |
| 7,049,378 B2 | 5/2006 | Ittel et al. | |
| 7,115,689 B2 | 10/2006 | Coalter, III et al. | |
| 7,157,400 B2 | 1/2007 | Boussie et al. | |
| 7,253,133 B2 | 8/2007 | Sun et al. | |
| 7,423,101 B2 | 9/2008 | Solan et al. | |
| 7,439,205 B2 | 10/2008 | Razavi et al. | |
| 2008/0177020 A1 | 7/2008 | Agapie et al. | |

OTHER PUBLICATIONS

Mao et al., Tetrahedron Letters, 2005, 46, 8419-8422.*
Bei et al., "Synthesis, Structures, Bonding, and Ethylene Reactivity of Group 4 Metal Alkyl Complexes Incorporating 8-Quinolinolato Ligands," *Organometallics*, (1997), 16, 3283-3302.
Mao et al., "New tridentate cyclometalated platinum(II) and palladium(II) complexes of N, 2-diphenyl-8-qunolinamine: syntheses, crystal structures, and photophysical properties," Tetrahedron Letters, (2005), 46, 8419-8422.
Ittel, et al., "Late-Metal Catalysts for Ethylene Homo- and Copolymerization," *Chem Rev. 100* (2000) 1169-1203.
Agapie et al., "Zirconium and Titanium Complexes Supported by Tridentate LX$_2$ Ligands Having Two Phenolates Linked to Furan, Thiophene, and Pyridine Donors: Precatalyts for Propylene Polymerization and Oligomerization," *Organometallics*, (2008), 27, 6245-6256.

* cited by examiner

*Primary Examiner*—Rip A. Lee
(74) *Attorney, Agent, or Firm*—Jonathan L. Schuchard

(57) ABSTRACT

Catalysts useful for polymerizing olefins are disclosed. The catalysts comprise an activator and a Group 4 metal complex that incorporates a dianionic, tridentate 2-aryl-8-anilinoquinoline ligand. In one aspect, supported catalysts are prepared by first combining a boron compound having Lewis acidity with excess alumoxane to produce an activator mixture, followed by combining the activator mixture with a support and the tridentate, dianionic Group 4 metal complex. The catalysts are easy to synthesize, support, and activate, and they enable facile production of high-molecular-weight polyolefins.

10 Claims, No Drawings

CATALYSTS BASED ON 2-ARYL-8-ANILINOQUINOLINE LIGANDS

FIELD OF THE INVENTION

The invention relates to non-metallocene catalysts useful for polymerizing olefins. The catalysts incorporate a tridentate dianionic ligand.

BACKGROUND OF THE INVENTION

While Ziegler-Natta catalysts are a mainstay for polyolefin manufacture, single-site (metallocene and non-metallocene) catalysts represent the industry's future. These catalysts are often more reactive than Ziegler-Natta catalysts, and they produce polymers with improved physical properties. The improved properties include controlled molecular weight distribution, reduced low molecular weight extractables, enhanced incorporation of α-olefin comonomers, lower polymer density, controlled content and distribution of long-chain branching, and modified melt rheology and relaxation characteristics.

Traditional metallocenes incorporate one or more cyclopentadienyl (Cp) or Cp-like anionic ligands such as indenyl, fluorenyl, or the like, that donate pi-electrons to the transition metal. Non-metallocene single-site catalysts, including ones that capitalize on the chelate effect, have evolved more recently. Examples are the bidentate 8-quinolinoxy or 2-pyridinoxy complexes of Nagy et al. (see U.S. Pat. No. 5,637,660), the late transition metal bisimines of Brookhart et al. (see *Chem. Rev.* 100 (2000) 1169), and the diethylenetriamine-based tridentate complexes of McConville et al. or Shrock et al. (e.g., U.S. Pat. Nos. 5,889,128 and 6,271,323).

In numerous recent examples, the bi- or tridentate complex incorporates a pyridyl ligand that bears a heteroatom β- or γ- to the 2-position of the pyridine ring. This heteroatom, typically nitrogen or oxygen, and the pyridyl nitrogen chelate the metal to form a five- or six-membered ring. For some examples, see U.S. Pat. Nos. 7,439,205; 7,423,101; 7,157,400; 6,653,417; and 6,103,657 and U.S. Pat. Appl. Publ. No. 2008/0177020. In some of these complexes, an aryl substituent at the 6-position of the pyridine ring is also available to interact with the metal through C—H activation to form a tridentate complex (see, e.g., U.S. Pat. Nos. 7,115,689; 6,953,764; 6,706,829). Unfortunately, some of these complexes are tricky to prepare, and they are most useful unsupported; our own attempts to prepare similar complexes and support them on silica, for example, met with mixed results.

Less frequently, quinoline-based bi- or tridentate complexes have been described (see, e.g., U.S. Pat. Nos. 7,253,133; 7,049,378; 6,939,969; 6,103,657; 5,637,660 and *Organometallics* 16 (1997) 3282). The quinoline complexes disclosed in the art lack an 8-anilino substituent, a 2-aryl substituent, or both, and/or they are not dianionic and tridentate.

New non-metallocene catalysts useful for making polyolefins continue to be of interest. In particular, tridentate complexes that can be readily synthesized from inexpensive reagents are needed. The complexes should not be useful only in homogeneous environments; a practical complex can be supported on silica and readily activated toward olefin polymerization with alumoxanes or boron-containing cocatalysts. Ideally, the catalysts have the potential to make ethylene copolymers having high or very high molecular weights and can be utilized in high-temperature solution polymerizations.

SUMMARY OF THE INVENTION

The invention relates to catalysts useful for polymerizing olefins. The catalysts comprise an activator and a Group 4 metal complex. The complex incorporates a dianionic, tridentate 2-aryl-8-anilinoquinoline ligand. In one aspect, a supported catalyst is prepared by first combining a boron compound having Lewis acidity with excess alumoxane to produce an activator mixture, followed by combining the activator mixture with a support and the dianionic, tridentate Group 4 metal complex. The catalysts are easy to synthesize, support, and activate, and they enable facile production of high-molecular-weight polyolefins.

DETAILED DESCRIPTION OF THE INVENTION

Catalysts of the invention are particularly useful for polymerizing olefins. They comprise an activator and a Group 4 transition metal complex. Group 4 metals include zirconium, titanium, and hafnium. Zirconium and titanium are particularly preferred.

The catalysts include one or more activators. The activator helps to ionize the complex and activate the catalyst. Suitable activators are well known in the art. Examples include alumoxanes (methyl alumoxane (MAO), PMAO, ethyl alumoxane, diisobutyl alumoxane), alkylaluminum compounds (triethylaluminum, diethylaluminum chloride, trimethylaluminum, triisobutylaluminum), and the like. Suitable activators include boron and aluminum compounds having Lewis acidity such as ionic borates or aluminates, organoboranes, organoboronic acids, organoborinic acids, and the like. Specific examples include lithium tetrakis(pentafluorophenyl)borate, lithium tetrakis(pentafluorophenyl)aluminate, anilinium tetrakis(pentafluorophenyl)-borate, trityl tetrakis(pentafluorophenyl)borate ("F20"), tris(pentafluorophenyl)-borane ("F15"), triphenylborane, tri-n-octylborane, bis(pentafluorophenyl)borinic acid, pentafluorophenylboronic acid, and the like. These and other suitable boron-containing activators are described in U.S. Pat. Nos. 5,153,157, 5,198,401, and 5,241,025, the teachings of which are incorporated herein by reference. Suitable activators also include aluminoboronates—reaction products of alkyl aluminum compounds and organoboronic acids—as described in U.S. Pat. Nos. 5,414,180 and 5,648,440, the teachings of which are incorporated herein by reference. Particularly preferred activators are alumoxanes, boron compounds having Lewis acidity, and mixtures thereof.

In addition to the Group 4 metal, the complex includes a dianionic, tridentate 2-aryl-8-anilinoquinoline ligand. The ligand is "tridentate" and "dianionic" in that it binds to the metal with two anionic sites and one neutral site. The neutral site is the tertiary amine group of the quinoline moiety. The anionic sites are a nitrogen anion derived from the 8-anilino substituent and a carbanion derived from the 2-aryl substituent.

Preferred complexes have the structure:

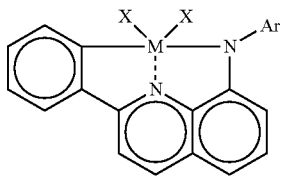

in which M is a Group 4 transition metal, Ar is an aryl group, each X is independently selected from the group consisting of halide, amide, alkyl, aryl, and alkaryl, and any of the ring carbons is optionally substituted with an alkyl, aryl, halide, alkoxy, trialkylsilyl, dialkylamino, or haloalkyl group, or any pair of adjacent ring carbons are joined to form a 5 to 7-membered carbocyclic or heterocyclic ring.

Particularly preferred complexes have the structure:

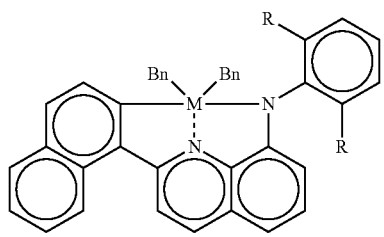

in which Bn is benzyl and each R is independently selected from the group consisting of methyl, ethyl, n-propyl, isopropyl, n-butyl, and tert-butyl.

A few other exemplary complexes:

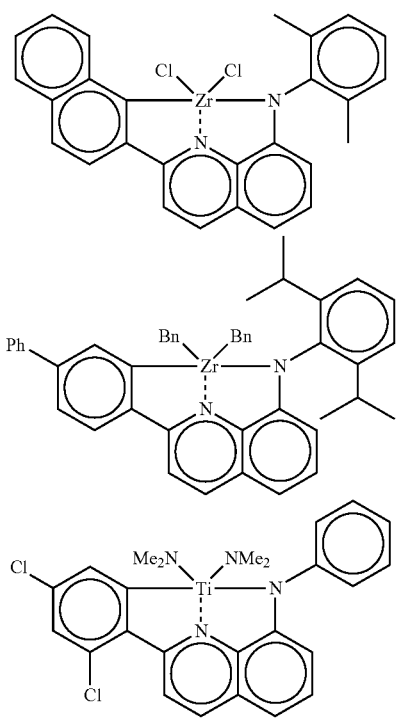

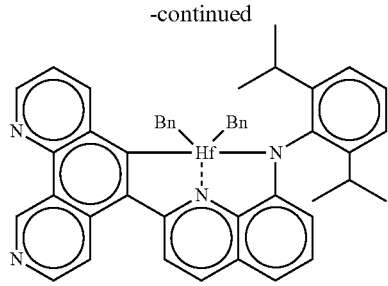

The catalysts are preferably supported on an inorganic oxide such as silica, alumina, silica-alumina, magnesia, titania, zirconia, clays, zeolites, or the like. Silica is preferred. When silica is used, it preferably has a surface area in the range of 10 to 1000 $m^2/g$, more preferably from 50 to 800 $m^2/g$ and most preferably from 200 to 700 $m^2/g$. Preferably, the pore volume of the silica is in the range of 0.05 to 4.0 mL/g, more preferably from 0.08 to 3.5 mL/g, and most preferably from 0.1 to 3.0 mL/g. Preferably, the average particle size of the silica is in the range of 1 to 500 microns, more preferably from 2 to 200 microns, and most preferably from 2 to 45 microns. The average pore diameter is typically in the range of 5 to 1000 angstroms, preferably 10 to 500 angstroms, and most preferably 20 to 350 angstroms.

The support is preferably treated thermally, chemically, or both prior to use by methods well known in the art to reduce the concentration of surface hydroxyl groups. Thermal treatment consists of heating (or "calcining") the support in a dry atmosphere at elevated temperature, preferably greater than 100° C., and more preferably from 150 to 800° C., prior to use. A variety of different chemical treatments can be used, including reaction with organo-aluminum, -magnesium, -silicon, or -boron compounds. See, for example, the techniques described in U.S. Pat. No. 6,211,311, the teachings of which are incorporated herein by reference.

Highly active non-metallocene catalysts of the invention can be made by using a particular sequence for activating and supporting the tridentate dianionic complexes. One method of preparing a supported catalyst useful for polymerizing olefins comprises two steps. In a first step, a boron compound having Lewis acidity (as described earlier) is combined with excess alumoxane, preferably methylalumoxane, to produce an activator mixture. In a second step, the resulting activator mixture is combined with a support, preferably silica, and a complex which comprises a Group 4 transition metal and a dianionic, tridentate 2-aryl-8-anilinoquinoline ligand. In one approach, the activator mixture is combined with the complex first, followed by the support. However, the order can be reversed; thus, the activator mixture can be combined with the support first, followed by the complex.

In a typical example, the boron compound is combined with excess MAO in a minimal amount of a hydrocarbon. The complex is added and the combined mixture is then added to a large proportion of calcined silica in an incipient wetness technique to provide the supported catalyst as a free-flowing powder.

As the results in Table 1 (below) show, various ways of supporting the complex can be used to provide an active catalyst. In particular, Method D generally provides non-metallocene catalysts with excellent activity. Compare the activity results of supported catalysts made by Method D, Example 3 (with complex 39) versus Method A, Examples 5 and 6 (MAO-treated silica, slurry technique, no borate) and Method C, Example 7 (incipient wetness technique, borate but no MAO). The increase in activity from Method D with these complexes is substantial and unexpected.

Table 2 shows that catalysts of the invention perform well with a wide range of boron compounds having Lewis acidity. In addition to F20 (an ionic borate, Examples 4 and 8), good activities result from using a triarylborane (Ex. 9), a borinic acid (Ex. 10), or a boronic acid (Ex. 11) in combination with excess MAO.

Table 3 shows that the high molecular weight typically obtained for olefin copolymers is successfully controlled by introducing hydrogen. Thus, the supported catalysts have good hydrogen sensitivity. As an added bonus, activity increases to a sustained, high level with even greater hydrogen levels.

Comparative Examples 18 and 19 show the performance of catalysts made using a tridentate dianionic complex that incorporates a 2,6-disubstituted pyridine ligand as described in U.S. Pat. No. 7,157,400. These complexes are somewhat more challenging to synthesize compared with the 2-aryl-8-anilinoquinoline complexes of the invention because they generally require higher temperatures and longer reaction times. Moreover, as shown in the examples, the quinoline complexes are more active (see Example 5 and Comparative Example 18, both made using Zr complexes and supporting Method A).

The invention includes processes for polymerizing olefins. In one process, at least one of ethylene, propylene, and an α-olefin is polymerized in the presence of a catalyst of the invention. Preferred α-olefins are $C_4$-$C_{20}$ α-olefins such as 1-butene, 1-hexene, 1-octene, and the like. Ethylene and mixtures of ethylene with propylene or a $C_4$-$C_{10}$ α-olefin are particularly preferred. Most preferred are polymerizations of ethylene with 1-butene, 1-hexene, 1-octene, and mixtures thereof.

Many types of olefin polymerization processes can be used. Preferably, the process is practiced in the liquid phase, which can include slurry, solution, suspension, or bulk processes, or a combination of these. High-pressure fluid phase or gas phase techniques can also be used. In a preferred olefin polymerization process, a supported catalyst of the invention is used. The polymerizations can be performed over a wide temperature range, such as −30° C. to 280° C. A more preferred range is from 30° C. to 180° C.; most preferred is the range from 60° C. to 100° C. Olefin partial pressures normally range from 15 psig to 50,000 psig. More preferred is the range from 15 psig to 1000 psig.

The invention includes a high-temperature solution polymerization process. By "high-temperature," we mean at a temperature normally used for solution polymerizations, i.e., preferably greater than 130° C., and most preferably within the range of 135° C. to 250° C. Example 20 demonstrates that the tridentate dianionic complexes of the invention perform well in a typical high-temperature solution polymerization and can provide olefin polymers, particularly polyethylenes, having desirably high molecular weights.

The following examples merely illustrate the invention. Those skilled in the art will recognize many variations that are within the spirit of the invention and scope of the claims.

All intermediate compounds and complexes synthesized give satisfactory $^1$H NMR spectra consistent with the structures indicated.

Preparation of Complex 36

8-Bromo-2-(1-naphthyl)quinoline

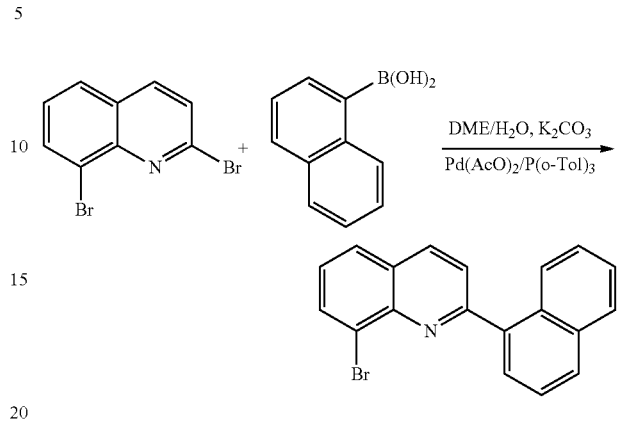

A mixture of 2,8-dibromoquinoline (6.0 g, 21 mmol, prepared by the method of L. Mao et al., Tetrahedron Lett. 46 (2005) 8419), 1-naphthylboronic acid (4.1 g, 24 mmol), $K_2CO_3$ (6.6 g, 48 mmol), Pd(OAc)$_2$ (0.1 g, 0.4 mmol), P(o-Tol)$_3$ (0.25 g, 0.8 mmol), DME (50 mL) and water (10 mL) is refluxed for 6 h under stirring in an argon atmosphere. The mixture is then poured into water and extracted with CHCl$_3$ (3×50 mL). The combined organic phase is washed with water and brine, and then concentrated. The residue is purified by column chromatography (silica gel 40, hexane/benzene 1:1). Yield of red purple oil: 4.1 g (57%).

N-(2,6-dimethylphenyl)-2-(1-naphthyl)-8-quinolinamine

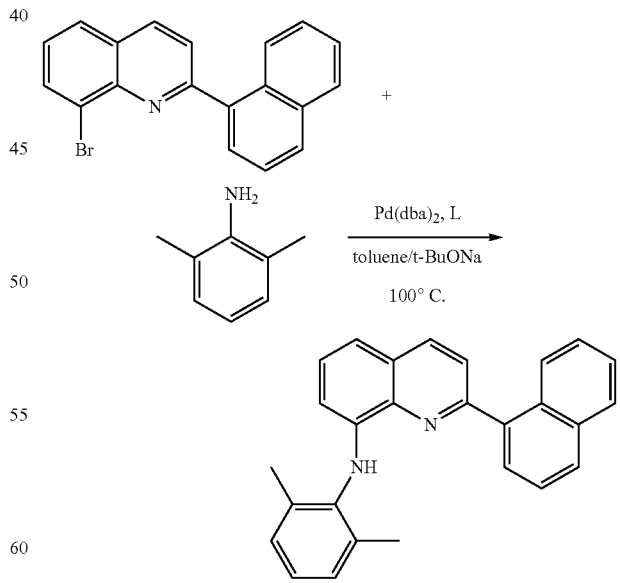

A mixture of 8-bromo-2-(1-naphthyl)quinoline (2.03 g, 6 mmol), 2,6-dimethylaniline (0.83 mL, 6.9 mmol), Pd(dba)$_2$ (0.072 g, 0.12 mmol), L=(N-[2'-(dicyclohexylphosphino)[1,1'-biphenyl]-2-yl]-N,N-dimethylamine) (0.094 g, 0.24 mmol), NaOtBu (0.72 g, 7.2 mmol) and toluene (15 mL) is stirred for 8 h under an argon atmosphere at 100° C. in an oil bath. The mixture is then poured into water and extracted with benzene (3×50 mL). The combined organic phase is washed with water and brine, and then concentrated. The residue is purified by column chromatography (silica gel 40, hexane/toluene 2:1). Yield: 1.59 g (71%).

Dibenzylzirconium N-(2,6-Dimethylphenyl)-2-(1-naphthyl)-8-quinolinamide (36)

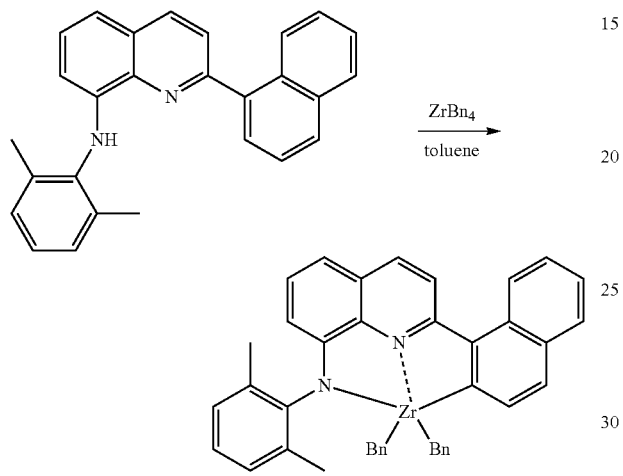

A solution of tetrabenzylzirconium (1.10 g, 2.4 mmol) in toluene (10 mL) is added at 0° C. to a solution of N-(2,6-dimethylphenyl)-2-(1-naphthyl)-8-quinolinamine (0.75 g, 2 mmol) in toluene (20 mL). The color of the mixture changes from pale yellow to dark red. The resulting mixture is allowed to warm to room temperature and is then stirred for 4 h at 50° C. The mixture is concentrated to about 10 mL, and hexane (20 mL) is added. The crystalline precipitate is separated by decantation, washed with pentane, and dried in vacuo. Yield of 36, a red-violet crystalline powder: 0.74 g (57%). $^1$H NMR (toluene-$d_8$) δ: 8.40 (d, 1H); 8.08 (d, 1H); 7.99 (d, 1H); 7.69 (t, 2H); 7.56 (d, 1H); 7.40-7.27 (m, 4H); 7.17-6.96 (m, 3H); 6.64 (m, 4H); 6.56 (m, 2H); 6.41 (m, 4H); 6.21 (d, 1H); 2.33 (d, 2H); 2.18 (s, 3H); 2.13 (s, 3H); 1.83 (d, 2H).

Preparation of Complex 37

Dibenzylhafnium N-(2,6-Dimethylphenyl)-2-(1-naphthyl)-8-quinolin-amide (37)

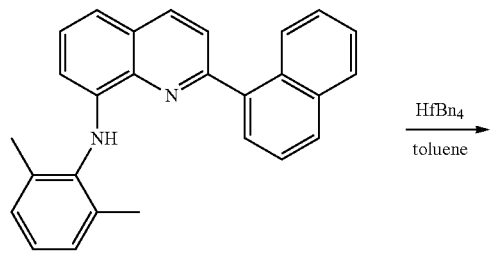

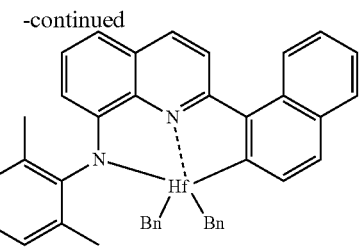

A solution of tetrabenzylhafnium (1.14 g, 2.1 mmol) in toluene (10 mL) is added at 0° C. to a solution of N-(2,6-dimethylphenyl)-2-(1-naphthyl)-8-quinolinamine (0.65 g, 1.75 mmol) in toluene (15 mL). The color of the mixture changes from pale yellow to red. The resulting mixture is allowed to warm to room temperature and is then stirred for 8 h at 60° C. The mixture is concentrated to about 10 mL, and hexane (20 mL) is added. The crystalline precipitate is separated by decantation, washed with pentane, and dried in vacuo. Yield of 37, a red crystalline powder: 0.81 g (63%).

Preparation of Complex 38

Dibenzylhafnium N-(2,6-Diisopropylphenyl)-2-(1-naphthyl)-8-quinolinamide (38)

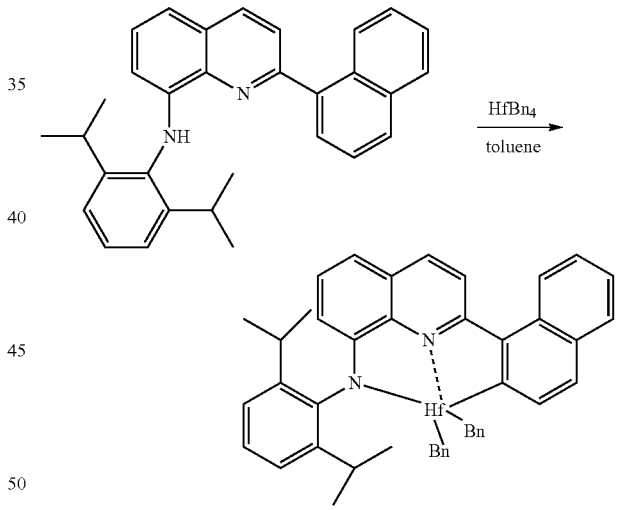

A solution of tetrabenzylhafnium (1.17 g, 2.15 mmol) in toluene (10 mL) is added at 0° C. to a solution of N-(2,6-diisopropylphenyl)-2-(1-naphthyl)-8-quinolinamine (0.69 g, 1.6 mmol) in toluene (15 mL). The color of the mixture changes from pale yellow to red. The resulting mixture is allowed to warm to room temperature and is then stirred for 8 h at 60° C. The mixture is concentrated to about 10 mL, and hexane (20 mL) is added. The crystalline precipitate is separated by decantation, washed with pentane, and dried in vacuo. Yield of 38, a red crystalline powder: 0.68 g (54%). $^1$H NMR (benzene-$d_6$) δ: 8.22 (d, 1H); 8.12 (d, 1H); 7.71 (d, 1H); 7.57 (m, 2H); 7.40 (d, 1H); 7.16 (m, 4H); 7.00 (m, 2H); 6.67 (d, 1H); 6.52-6.36 (m, 10H); 6.10 (d, 1H); 3.41 (sept, 2H); 2.26 (d, 2H); 2.03 (d, 2H); 1.10 (d, 6H); 0.88 (d, 6H).

Preparation of Complex 39

N-(2,6-Diisopropylphenyl)-2-(1-naphthyl)-8-quinolinamine

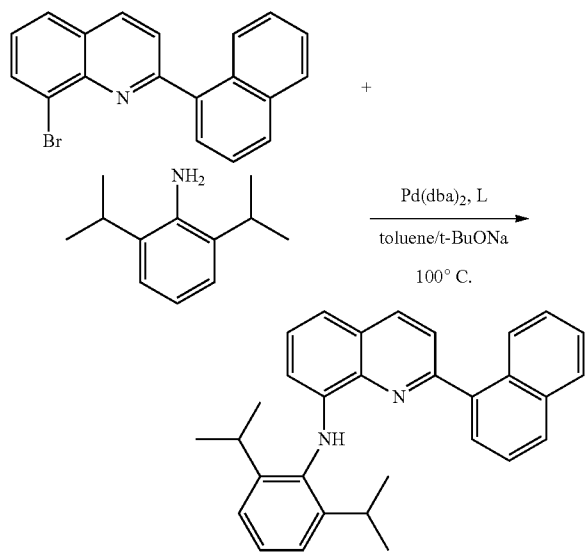

A mixture of 8-bromo-2-(1-naphthyl)quinoline (2.03 g, 6 mmol), 2,6-diisopropylaniline (1.3 ml, 7 mmol), Pd(dba)$_2$ (72 mg, 0.12 mmol), L=(N-[2'-(dicyclohexylphosphino)[1,1'-biphenyl]-2-yl]-N,N-dimethylamine (94 mg, 0.24 mmol), Nad$^t$Bu (0.72 g, 7.2 mol) and toluene (15 mL) is stirred for 8 h under an argon atmosphere at 105° C. in an oil bath. The mixture is then poured into water and extracted with benzene (3×50 mL). The combined organic phase is washed with water and brine, and is then concentrated. The residue is purified by column chromatography (silica gel 40, hexane/toluene 2:1). Yield: 1.7 g (66%).

Dibenzylzirconium N-(2,6-Diisopropylphenyl)-2-(1-naphthyl)-8-quinolinamide (39)

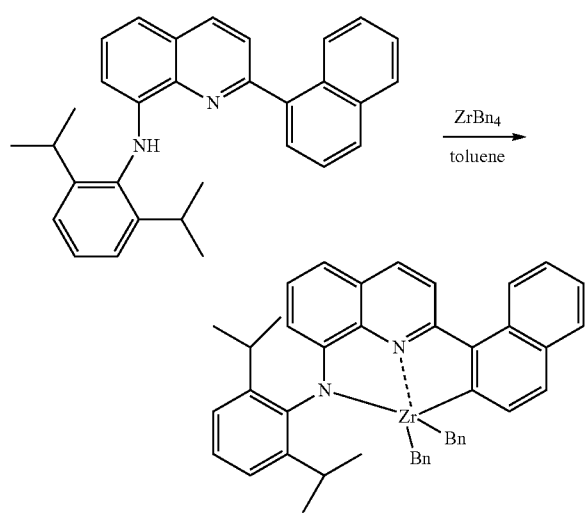

A solution of tetrabenzylzirconium (1.23 g, 2.7 mmol) in toluene (10 mL) is added at 0° C. to a solution of N-(2,6-diisopropylphenyl)-2-(1-naphthyl)-8-quinolinamine (0.95 g, 2.2 mmol) in toluene (20 mL). The color of the mixture changes from pale yellow to dark red. The resulting mixture is allowed to warm to room temperature and is then stirred for 8 h at 60° C. Toluene is evaporated, and the residue is extracted with pentane. The product crystallizes very slowly! Yield of 39, a red-violet crystalline powder: 0.55 g (36%). $^1$H NMR (toluene-d$_8$) δ: 8.31 (d, 1H); 8.11 (d, 1H); 7.94 (d, 1H); 7.68 (t, 2H); 7.55 (d, 1H); 7.29 (m, 4H); 7.14 (m, 2H); 6.96 (m, 1H); 6.64 (m, 4H); 6.52 (m, 6H); 6.26 (d, 1H); 3.49 (sept, 2H); 2.50 (d, 2H); 2.01 (d, 2H); 1.26 (d, 6H); 1.05 (d, 6H).

Preparation of Complex 44

N-(2-Methyl-1-naphthyl)-2-(1-naphthyl)-8-quinolinamine

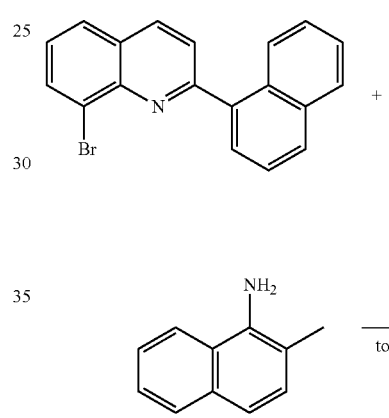

A mixture of 8-bromo-2-(1-naphthyl)quinoline (3.25 g, 9.7 mmol), 2-methyl-1-naphthalenamine (1.76 g, 11.2 mmol), Pd(dba)$_2$ (0.12 g, 0.2 mmol), L=(N-[2'-(dicyclohexylphosphino)[1,1'-biphenyl]-2-yl]-N,N-dimethylamine (0.15 g, 0.4 mmol), NaO$^t$Bu (1.15 g, 12 mmol) and toluene (20 mL) is stirred for 8 h under an argon atmosphere at 100° C. in oil bath. The mixture is then poured into water and extracted with benzene (3×40 mL). The combined organic phases are washed with water and brine and then concentrated. The residue is purified by column chromatography (silica gel 40, hexane/toluene 4:1). Yield 3.1 g (78%).

Dibenzylzirconium N-(2-Methyl-1-naphthyl)-2-(1-naphthyl)-8-quinolinamide (44)

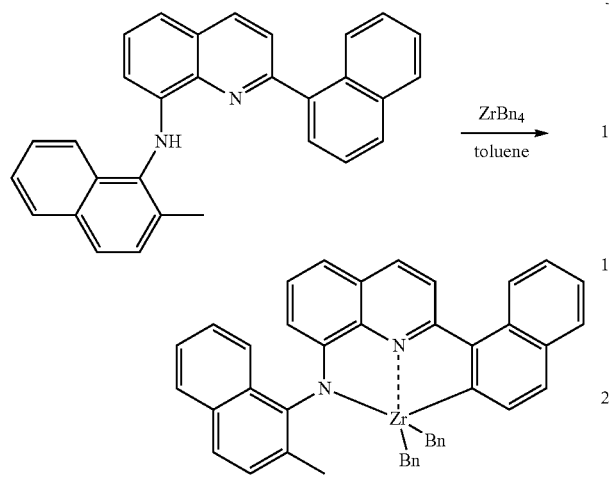

A solution of tetrabenzylzirconium (0.51 g, 1.12 mmol) in toluene (5 mL) is added at 0° C. to a solution of N-(2,6-diisopropylphenyl)-2-(1-naphthyl)-8-quinolinamine (0.37 g, 0.9 mmol) in toluene (15 mL). The color of the mixture changes from pale yellow to dark red. The resulting mixture is allowed to warm to room temperature and is then stirred for 8 h at 60° C. Toluene is evaporated, and the residue is extracted with pentane and crystallized. Yield of 44, a dark red-violet crystalline powder: 0.28 g (46%). $^1$H NMR (toluene-$d_8$) δ: 8.44 (d, 1H); 8.06 (d, 1H); 8.01 (d, 1H); 7.95 (d, 1H); 7.74 (d, 1H); 7.69 (m, 1H); 7.65 (d, 1H); 7.50 (d, 1H); 7.39-7.21 (m, 5H); 6.57 (m, 3H); 6.40 (m, 3H); 6.32 (m, 2H); 6.26 (m, 2H); 6.1 (d, 1H); 2.34 (d, 1H); 2.30 (s, 3H); 2.29 (d, 1H); 1.75 (d, 1H); 1.59 (d, 1H).

Preparation of Supported Catalysts

Method A

A mixture of silica (Davison 948, calcined at 250° C. for 4 h, 2.0 g), methylalumoxane (30 wt. % solution of MAO in toluene, product of Albemarle, 2.2 mL), and toluene (10 mL) is stirred under nitrogen for 1 h at 80° C. The resulting slurry is cooled to ambient temperature, and a specified amount of catalyst precursor is added, dry or in toluene solution, under stirring. After 30 min., the slurry is filtered and the solids are rinsed with hexanes (2×5 mL) and dried. The resulting catalyst is used in polymerization tests.

Method C

A specified amount of complex precursor is added to a solution of a specified amount of trityl tetrakis(pentafluorophenyl)borate in toluene (2.2 mL). The mixture is stirred at ambient temperature for 15 min. Thereafter, the mixture is slowly added to a stirred bed of silica (Davison 948, calcined at 600° C. for 6 h, 2.0 g). The resulting free-flowing powder is used in polymerization tests.

Method D

Trityl tetrakis(pentafluorophenyl)borate ("F20," 0.093 g) is added to methylalumoxane (30 wt. % solution of MAO in toluene, 2.0 mL), and the mixture is stirred for 15 min. A specified amount of complex precursor is added to the MAO/borate solution, and the mixture stirs for an additional 15 min. The resulting product is slowly added to a stirred bed of silica (Davison 948, calcined at 600° C. for 6 h, 2.0 g). The resulting free-flowing powder is used in polymerization tests.

Ethylene Polymerization

General Procedure

A dry, 2-L stainless-steel autoclave is charged with isobutane (1.0 L), triisobutylaluminum (1 M solution in hexanes, 2 mL), 1-butene (100 mL) and, optionally, hydrogen, and the contents are heated to 70° C. and pressurized with ethylene (15.5 psi partial pressure). Polymerization is started by injecting the catalyst with a small quantity of isobutane. The temperature is maintained at 70° C., and ethylene is supplied on demand throughout the test. The reaction is terminated by cooling the reactor and venting its contents.

Polymerization Example 1, for instance, uses a catalyst batch prepared using Method D and complex 36 (31.6 mg) resulting in an Al/B/Zr ratio of 190/1.2/1. A sample of catalyst corresponding to 5.2 mg of the complex is used in the polymerization test. The test yields 36.3 g of high molecular weight ethylene/butene copolymer in 56 minutes (activity: 4824 kg/mol Zr/h). Polymerization Exs. 2-7 are performed analogously. Results appear in Table 1.

TABLE 1

Polymerization Results

| Ex | Complex, amt (mg) | Support method | Al/B/M (molar) | Complex in test (mg) | Polymer yield | Time (min) | Activity (kg/mol M/h) |
|---|---|---|---|---|---|---|---|
| 1 | 36 (31.6) | D | 190/1.2/1 | 5.2 | 36.3 | 56 | 4824 |
| 2 | 38 (38.7) | D | 190/1.2/1 | 5.0 | 8.8 | 78 | 1067 |
| 3 | 39 (34.3) | D | 190/1.2/1 | 5.0 | 36.8 | 77 | 5113 |
| 4 | 44 (33.4) | D | 190/1.2/1 | 5.0 | 32.2 | 90 | 2925 |
| 5 | 39 (58.0) | A | 100/0/1 | 3.0 | 8.1 | 56 | 2030 |
| 6 | 39 (19.0) | A | 300/0/1 | 6.0 | 34.8 | 60 | 4066 |
| 7 | 39 (65.0) | C | 0/4/1 | 2.1 | 3.6 | 92 | 783 |

Polymerization Examples 8-11

Effect of Other Boron Activators

Method D is used to make supported catalysts from complex 44, MAO, and the boron compounds shown in Table 2. The procedure of Polymerization Example 4 is generally followed except that hydrogen (0.085 moles) is used. Activities are shown in Table 2.

Polymerization Example 12

Method A is used to make a supported catalyst from complex 44, except that the silica is calcined at 600° C. The polymerization is performed in the absence of hydrogen, and with only MAO as the activator. Activity: 871 kg/mol Zr/h.

TABLE 2

Effect of Boron Activators with Complex 44

| Ex. # | Activator = MAO + . . . | Al/B/Zr (molar) | $H_2$, moles | Activity (kg/mol Zr/h) |
|---|---|---|---|---|
| 4 | $Ph_3C + B(C_6F_5)_4^-$ | 190/1.2/1 | 0 | 2925 |
| 8 | $Ph_3C + B(C_6F_5)_4^-$ | 190/1.2/1 | 0.085 | 5751 |
| 9 | $B(C_6F_5)_3$ | 190/1.2/1 | 0.085 | 7082 |
| 10 | $(C_6F_5)_2BOH$ | 190/1.4/1 | 0.085 | 5448 |
| 11 | $(C_6F_5)B(OH)_2$ | 190/1.4/1 | 0.085 | 9560 |
| 12 | no boron activator | 100/0/1 | 0 | 871 |

Polymerization Examples 13-17

Effect of Hydrogen

Method D is used to make supported catalysts from complex 39. Polymerizations are performed in the presence of different amounts of hydrogen and enough supported catalyst to deliver 5.0 mg of complex. No hydrogen is used in Example 13, which essentially repeats Example 3.

Polymerization Example 14, for instance, uses a 7-cm³ stainless-steel cylinder charged to 500 psi with hydrogen, and hydrogen is delivered to the reactor until the pressure in the cylinder drops by to 300 psi, i.e., the change in pressure is 200 psi. Examples 15-17 are analogous. Results appear in Table 3.

TABLE 3

Effect of Hydrogen with Complex 39

| Ex. # | $H_2$ cylinder vol. (cm³) | Amt. $H_2$ (Δ psi) | Polymer yield (mg) | Time (min) | Activity (kg/mol Zr/h) | Mw |
|---|---|---|---|---|---|---|
| 13 | — | — | 46.9 | 77 | 5118 | not soluble |
| 14 | 7 | 200 | 41.3 | 36 | 9643 | 804,000 |
| 15 | 7 | 400 | 47.6 | 36 | 11,116 | 507,000 |
| 16 | 300 | 40 | 80.5 | 60 | 11,288 | — |
| 17 | 300 | 100 | 68.2 | 54 | 10,622 | — |

Comparative Polymerization Example 18

A catalyst batch is prepared using Method A and a reaction product of tetrabenzylzirconium (43.0 mg) and ligand precursor Z (43.0 mg), which is prepared using a modified version of the synthesis described in U.S. Pat. No. 7,157,400. Precursor Z is added to tetrabenzylzirconium in toluene (2 mL), and the mixture is stirred at room temperature for 15 min. This mixture is then combined with MAO-treated silica as described in Method A to give a 100/1 ratio of Al/Zr. A sample of catalyst corresponding to 3.0 mg of the complex is used in the polymerization test. The test yields 8.0 g of high molecular weight ethylene/butene copolymer in 82 minutes (activity: 663 kg/mol Zr/h).

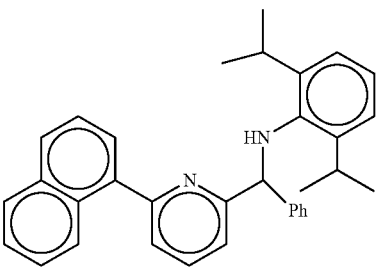

Precursor Z

Comparative Polymerization Example 19

The procedure of Comparative Polymerization Example 18 is repeated, except that tetrabenzylhafnium is used instead of tetrabenzylzirconium. The test yields no copolymer in 82 minutes (activity: 0 kg/mol Hf/h).

Polymerization Example 20:

High Temperature Solution Process

A silica-supported catalyst is prepared using Method D and complex 39 resulting in an Al/B/Zr ratio of 190/1.2/1. The catalyst (321 mg) is slurried in dry heptane (10 mL) in a glove box and stirred for about 1 h at room temperature.

Polymerizations are conducted in a 4-L semi-batch reactor which has a magnetically driven stirrer with 4 baffles. The polymer solution is rapidly discharged from the reactor via a dump valve into a receiving vessel that contains a BHT/MeOH mixture to kill the catalyst. In a typical polymerization, the reactor is charged with Isopar H (solvent), octene, hydrogen if used, then ethylene. Once a stable temperature and pressure are observed, triisobutylaluminum (TIBAL) is injected into the reactor followed immediately by the catalyst slurry. Run time starts when catalyst is injected and stops when the ethylene is shut off and the reactor is rapidly discharged to the collection vessel. Polymer slurry is isolated after cooling by filtration and drying in a vacuum oven at ~140° C. for >6 h.

Specific run conditions for this test: Isopar H solvent (1085 mL), 1-octene (300 mL), and ethylene are charged to a final reactor pressure of 500 psig. Reactor temperature: 140° C. TIBAL (1.0 mL of 1 M solution) and the catalyst slurry (8 mL) are added to catalyst and cocatalyst addition vessels. When the reactor has lined out at run conditions, TIBAL is injected followed 5 seconds later by the catalyst slurry. Polymerization continues for 15 min. to produce polyethylene. GPC characterization reveals a bimodal molecular weight distribution. Mn: 23,300; Mw: 225,700; Mz: 689,600; intrinsic viscosity: 2.57. DSC properties: melting point: 121° C.; heat of fusion: 96.0 J/g.

This data indicates excellent capability to produce high molecular weight polyethylene at a high polymerization temperature.

The preceding examples are meant only as illustrations. The following claims define the invention.

We claim:

1. A catalyst useful for polymerizing olefins, comprising an activator and a complex which comprises a Group 4 transition metal and a dianionic, tridentate 2-aryl-8-anilinoquinoline ligand.

2. The catalyst of claim 1 wherein the activator is selected from the group consisting of alumoxanes, boron compounds having Lewis acidity, and mixtures thereof.

3. The catalyst of claim 1 wherein the metal is zirconium or titanium.

4. The catalyst of claim 1 wherein the complex has the structure:

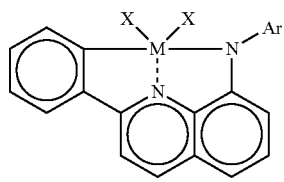

in which M is a Group 4 transition metal, Ar is an aryl group, each X is independently selected from the group consisting of halide, amide, alkyl, aryl, and alkaryl, and any of the ring carbons is optionally substituted with an alkyl, aryl, halide, alkoxy, trialkylsilyl, dialkylamino, or haloalkyl group, or any pair of adjacent ring carbons are joined to form a 5 to 7-membered carbocyclic or heterocyclic ring.

5. The catalyst of claim 4 wherein the complex has the structure:

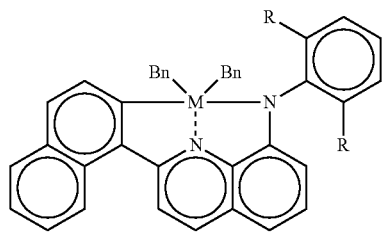

in which Bn is benzyl and each R is independently selected from the group consisting of methyl, ethyl, n-propyl, isopropyl, n-butyl, and tert-butyl.

6. A supported catalyst of claim 1.

7. A silica-supported catalyst of claim 2.

8. A process which comprises polymerizing at least one of ethylene, propylene, and an α-olefin in the gas, solution, or slurry phase in the presence of the catalyst of claim 1.

9. The process of claim 8 wherein the α-olefin is selected from the group consisting of 1-butene, 1-hexene, 1-octene, and mixtures thereof.

10. The process of claim 8 which comprises polymerizing in the solution phase at a temperature greater than 130° C.

* * * * *